(12) United States Patent
Altman et al.

(10) Patent No.: US 7,613,492 B2
(45) Date of Patent: Nov. 3, 2009

(54) APPARATUS FOR ALIGNING AN OBJECT BEING SCANNED IN MULTI-MODALITY SYSTEMS

(75) Inventors: Hernan Altman, Nesher (IL); Leonid Yakubovsky, Kiriat Bialik (IL); Sergio Steinfeld, Haifa (IL)

(73) Assignee: General Electric Company, Schenectady, NY (US)

( * ) Notice: Subject to any disclaimer, the term of this patent is extended or adjusted under 35 U.S.C. 154(b) by 729 days.

(21) Appl. No.: 10/898,781

(22) Filed: Jul. 26, 2004

(65) Prior Publication Data

US 2006/0036160 A1    Feb. 16, 2006

(51) Int. Cl.
*A61G 13/02* (2006.01)

(52) U.S. Cl. .............. 600/407; 600/411; 600/425; 600/427; 600/415; 5/601

(58) Field of Classification Search ............ 600/407, 600/425, 427, 436; 5/11, 601, 607, 610, 5/611, 630; 128/845; 378/20, 208, 209
See application file for complete search history.

(56) References Cited

U.S. PATENT DOCUMENTS

| | | | |
|---|---|---|---|
| 4,013,019 A * | 3/1977 | Horsey ............. | 108/5 |
| 5,497,776 A * | 3/1996 | Yamazaki et al. ..... | 600/445 |
| 5,615,430 A * | 4/1997 | Nambu et al. ........ | 5/600 |
| 5,891,030 A * | 4/1999 | Johnson et al. ....... | 600/407 |
| 5,971,767 A * | 10/1999 | Kaufman et al. ...... | 434/267 |
| 6,205,347 B1 | 3/2001 | Morgan et al. | |
| 6,211,523 B1 | 4/2001 | Gagnon | |
| 6,242,743 B1 | 6/2001 | DeVito et al. | |
| 6,399,951 B1 | 6/2002 | Paulus et al. | |
| 6,449,331 B1 | 9/2002 | Nutt et al. | |
| 6,490,476 B1 | 12/2002 | Townsend et al. | |
| 6,603,991 B1 | 8/2003 | Karmalawy et al. | |
| 6,631,284 B2 | 10/2003 | Nutt et al. | |
| 6,670,614 B1 | 12/2003 | Plut et al. | |
| 6,720,812 B2 | 4/2004 | Tumer et al. | |
| 6,754,519 B1 * | 6/2004 | Hefetz et al. ........ | 600/407 |
| 6,877,572 B2 * | 4/2005 | Vogel et al. ......... | 180/15 |
| 6,941,164 B2 * | 9/2005 | Hajaj et al. ......... | 600/407 |
| 6,994,067 B2 * | 2/2006 | Wallis .............. | 123/190.8 |
| 7,149,333 B2 * | 12/2006 | Pieper et al. ........ | 382/128 |
| 7,149,564 B2 * | 12/2006 | Vining et al. ....... | 600/425 |
| 2003/0105397 A1 | 6/2003 | Tumer et al. | |
| 2003/0128801 A1 | 7/2003 | Eisenberg et al. | |
| 2004/0210126 A1 * | 10/2004 | Hajaj et al. ........ | 600/407 |
| 2005/0023471 A1 | 2/2005 | Wang et al. | |

FOREIGN PATENT DOCUMENTS

JP    2000-102529    4/2000

* cited by examiner

*Primary Examiner*—Brian Casler
*Assistant Examiner*—Parikha S Mehta
(74) *Attorney, Agent, or Firm*—The Small Patent Law Group; Dean D. Small

(57) ABSTRACT

A method of examining a patient is provided. The method includes aligning a patient table with a first examination axis, and rotating the patient table around a substantially fixed pivot axis from the first examination axis to a second examination axis using a predetermined angular velocity profile.

16 Claims, 9 Drawing Sheets

APPARATUS FOR ALIGNING AN OBJECT BEING SCANNED IN MULTI-MODALITY SYSTEMS

BACKGROUND OF THE INVENTION

This invention relates generally to imaging and treatment systems capable of operation in multiple modalities, and more particularly to methods and apparatus for aligning an object being scanned in multi-modality systems.

Multi-modality imaging and treatment systems are capable of using different modalities, such as, for example, Positron Emission Tomography (PET), Single Positron emission tomography (SPECT), Ultrasound, Magnetic Resonance Imaging (MRI), Computed Tomography (CT), Static X-Ray imaging, Dynamic (Fluoroscopy) X-Ray imaging, and radiotherapy. In a multi-modality system (sometimes referred to as a multi-modal system), a portion of the same hardware is utilized to perform different scans or treatments, (e.g., an image produced by SPECT is processed and displayed respectively, by the same computer and display, as an image produced by CT). However, the data acquisition systems (also referred to as an "imaging assembly") are different. For example, on a CT/SPECT system, a radiation source and a radiation detector are used in combination to acquire CT data, while a radiopharmaceutical is typically employed in combination with a SPECT camera to acquire SPECT data.

In multi-modality systems, such as, for example, an integrated SPECT/CT system there is an inherent registration of the SPECT and CT images the system acquires. Because the patient lies motionless on the same table during the SPECT and CT portions of the acquisition, the patient will be in a consistent position and orientation during the two acquisitions, greatly simplifying the process of correlating and combining the CT and SPECT images. This allows the CT image to be used to provide attenuation correction information for the reconstruction of the SPECT image, and allows an image reader to easily correlate the anatomic information presented in the CT image and the functional information presented in the SPECT image.

This inherent registration assumes an alignment of the SPECT and CT detector coordinate systems, or at least a known spatial transformation between the two coordinate systems. A misalignment of the coordinate systems may directly result in a misregistration of the images. Misregistration results not only in inaccurate localization, but also to incorrect attenuation correction of the functional image.

Proper SPECT and CT image registration also requires an alignment of the axial (z-) axis of the SPECT and CT coordinate systems not only with each other, but also with the travel axis of the table that transports the patient between and during the SPECT and CT acquisitions. A co-axial SPECT/CT or other multi-modality system, especially for whole body scans, requires a relatively long axial travel distance to permit both imaging modalities the ability to image the region of interest. However, a patient table and table support may not be able to accommodate the alignment requirements while supporting a patient cantilevered out from the table support during an examination due to the extreme length of travel the patient table must travel to reach both imaging assemblies. For example, a co-axial imaging assembly arrangement requires a relatively long rail system, and the length of the bed may induce bending thereof, such that the patient position may change between the two imaging stations, even if the patient remains absolutely stationary. In non-coaxial systems the patient table is translated from a first examination axis to a second examination axis such that a patient may be moved, for example, shifted, with respect to the patient table or otherwise not be in the same position with respect to second examination axis as with the first examination axis.

BRIEF DESCRIPTION OF THE INVENTION

In one embodiment, a method of examining a patient is provided. The method includes aligning a patient table with a first examination axis, and rotating the patient table around a substantially fixed pivot axis from the first examination axis to a second examination axis using a predetermined angular velocity profile.

In another embodiment, an imaging system is provided. The imaging system includes at least a first and a second separate imaging assembly for obtaining medical diagnostic images of a patient for at least first and second imaging modalities, wherein the imaging assemblies are aligned along different first and second examination axis, a table configured to hold a patient during the first and the second examination, and a support mechanism configured to move the table between a first and a second examination position aligned with the first and second examination axes for corresponding first and a second imaging assemblies, the support mechanism comprising a positioner configured to engage a positioning socket to facilitate aligning the patient table with at least one of the first and second examination axes.

DETAILED DESCRIPTION OF THE INVENTION

Figure 1:
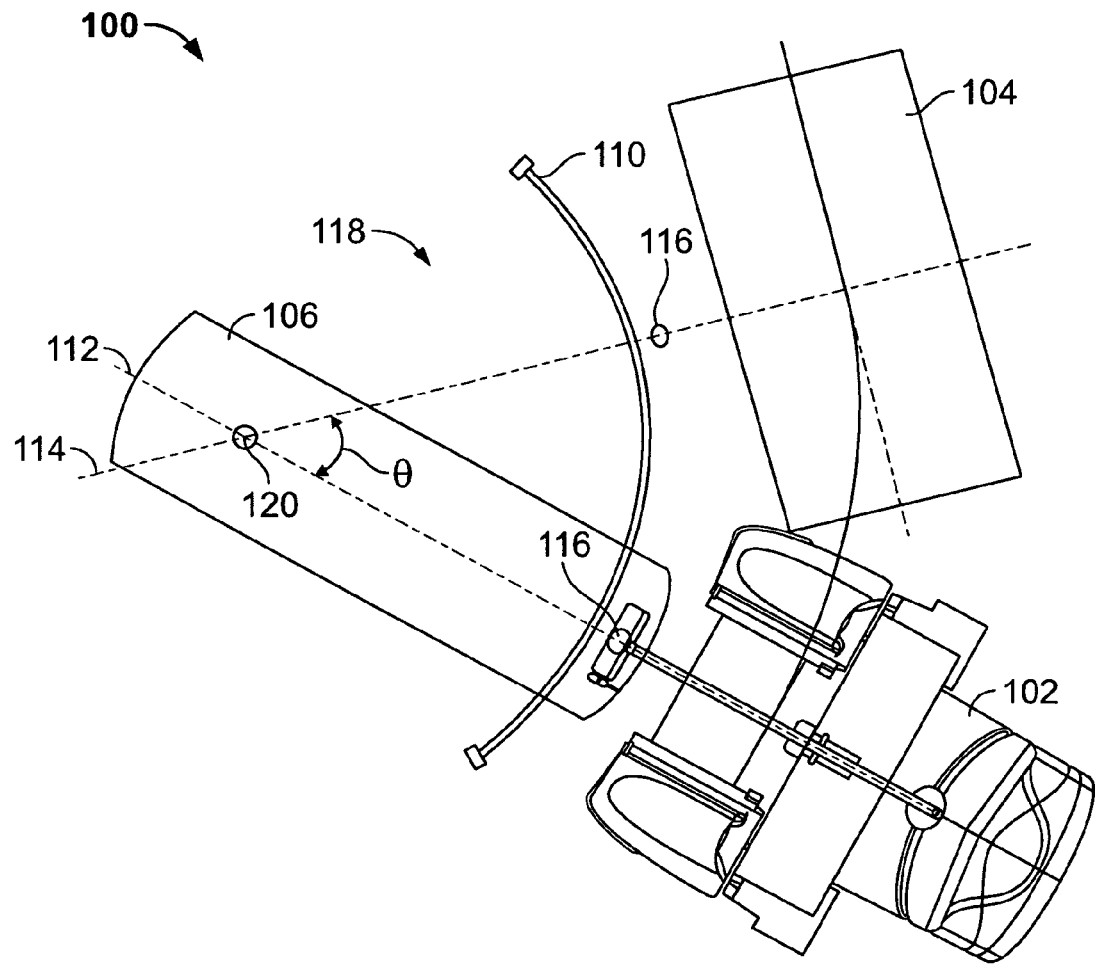
FIG. 1 is a schematic illustration of an imaging system in accordance with an exemplary embodiment of the present invention.

FIG. 1 is a schematic illustration of an exemplary embodiment of an imaging system 100. Imaging system 100 includes a first imaging assembly 102, a second imaging assembly 104, a patient table 106, and a support mechanism (not shown). In the exemplary embodiment, the support mechanism includes at least one guide member 110, such as, but, not limited to, a slot, a track, or a rail. Imaging assembly 102 includes an associated examination axis 112, and imaging assembly 104 includes an associated examination axis 114.

As used herein, each examination axis is referenced to a respective imaging apparatus used to image the patient. Guide member 110 is configured to engage a transport mechanism coupled to the support mechanism such that guided movement from examination axis 112 to examination axis 114 is controlled, and includes a positioner (not shown) to maintain the support mechanism in an aligned position along examination axis 112 and/or in an aligned position along examination axis 114. At least one positioner socket 116 may be fixed to a base 118, such as an examination room floor.

Each of imaging assemblies 102 and 104 may be, for example, any combination of a SPECT imaging assembly, a PET imaging assembly, a MRI imaging assembly, a CT imaging assembly, a Static X-Ray imaging assembly, a Dynamic (Fluoroscopy) X-Ray imaging assembly, and an ultrasound imaging assembly. Imaging assemblies 102 and 104 may be oriented such that examination axes 112 and 114 are angularly separated by an angle θ (theta).

In operation, a patient (not shown) may lie supine upon patient table 106 and aligned along examination axis 112. The support mechanism extends patient table 106, and a patient supported thereon, into imaging assembly 102 along examination axis 112 to perform a first imaging scan. The support mechanism retracts, patient table 106 to a predetermined stable position of the support mechanism and patient table 106. The support mechanism then pivots patient table 106 about angle θ such that patient table 106 is aligned with examination axis 114. The support mechanism extends patient table 106 and the patient into imaging assembly 104 along examination axis 114 to perform a second imaging scan, and thereafter retracts the patient table and the patient to a predetermined stable position of the support mechanism and patient table 106. Patient table 106 and each examination axis 112 and 114 are aligned during rotation about a pivot 120 of the support mechanism using one or more guide members 110 securely coupled to base 118, relative to imaging assemblies 102 and 104. After imaging the patient by imaging assembly 102, patient table 106 is unlocked from a position in alignment with examination axis 112, moved to a position in alignment with examination axis 114, and patient table 106 is then locked in position.

In operation, misregistration between imaging frames acquired using imaging assembly 102 and imaging assembly 104 is reduced by controlling an acceleration and angular velocity of the movement of patient bed 106 during rotation of patient bed 106 from a position in alignment with examination axis 112 to a position in alignment with examination axis 114. System 100 also may compensate for systemic and non-systemic misregistration. In the exemplary embodiment, system 100 is calibrated using a fiduciary marked phantom (not shown) positioned in a predetermined location on patient table 106 that is extended into a predetermined imaging position in first imaging assembly 102, such that a first imaging modality image is generated. Patient table 106 is retracted, moved along guide members 110 to examination axis 114, extended into imaging assembly 104, and a second imaging modality image is generated. The two images may be compared directly, and because the phantom is fixed in position on patient table 106 and does not move between the two imaging processes, this comparison enables correction data to be generated that can be used to calibrate the position and magnification of imaging assemblies 102 and 104 relative to the positions of patient table 106, such that their images produced refer to the same position of patient table 106.

In the exemplary embodiment, the correction data is used to physically adjust the position of patient table 106 relative to one or both of imaging assemblies 102 and 104, or vice versa, such as by means of automatic adjustment of patient bed 106 about angle θ and/or by raising or lowering patient table 106 with respect to base 118. In an alternative embodiment, no physical adjustment of the misalignment is performed, but the correction data is used to generate data for applying to one or both sets of the resulting images thereafter, to correct for misalignments. In another alternative embodiment, the correction data is used to physically adjust the position of patient table 106 relative to one or both of imaging assemblies 102 and 104, or vice versa, such as by means of automatic adjustment of patient bed 106 about angle θ and/or by raising or lowering patient table 106 with respect to base 118 to account for a gross misalignment, and a fine adjustment is applied to one or both sets of the resulting images thereafter, to correct for misalignments. Once pre-calibration is performed by any of these exemplary methods or others, when used on patients, all of the imaging systems of the multi-modality imaging system can then refer directly to the image details as if on an equivalently localized table, because the correlation between the table localization in the two systems is known. In an alternative embodiment, the fiduciary marked phantom may be integrated into patient table 106. For example, a plurality of indentations or holes may be formed in a surface of patient table 106 wherein the first modality, such as the CT imaging modality, is capable of viewing the indentations or holes. One or more radioactive sources may be positioned within the indentations or holes such that the one or more radioactive sources may be imaged by a second imaging modality, such as, a SPECT or PET imaging modality.

In operation, non-systemic registration may be affected by factors that may change between each image acquisition, for example, patient dependent factors such as patient weight and patient position on patient table 106. Differential non-systemic misregistration may reduced by maintaining substantially identical conditions of patient table 106 and support mechanism 108 between scans, such that the non-systemic misregistration for both imaging modalities may be ignored, for example, the misregistration is insignificant. Such substantially identical conditions of patient table 106 and the support mechanism between scans is provided by controlling the acceleration and angular velocity of patient table 106 during movement between a position in alignment with examination axis 112 and a position in alignment with examination axis 114, as described in more detail herein.

Figure 2:
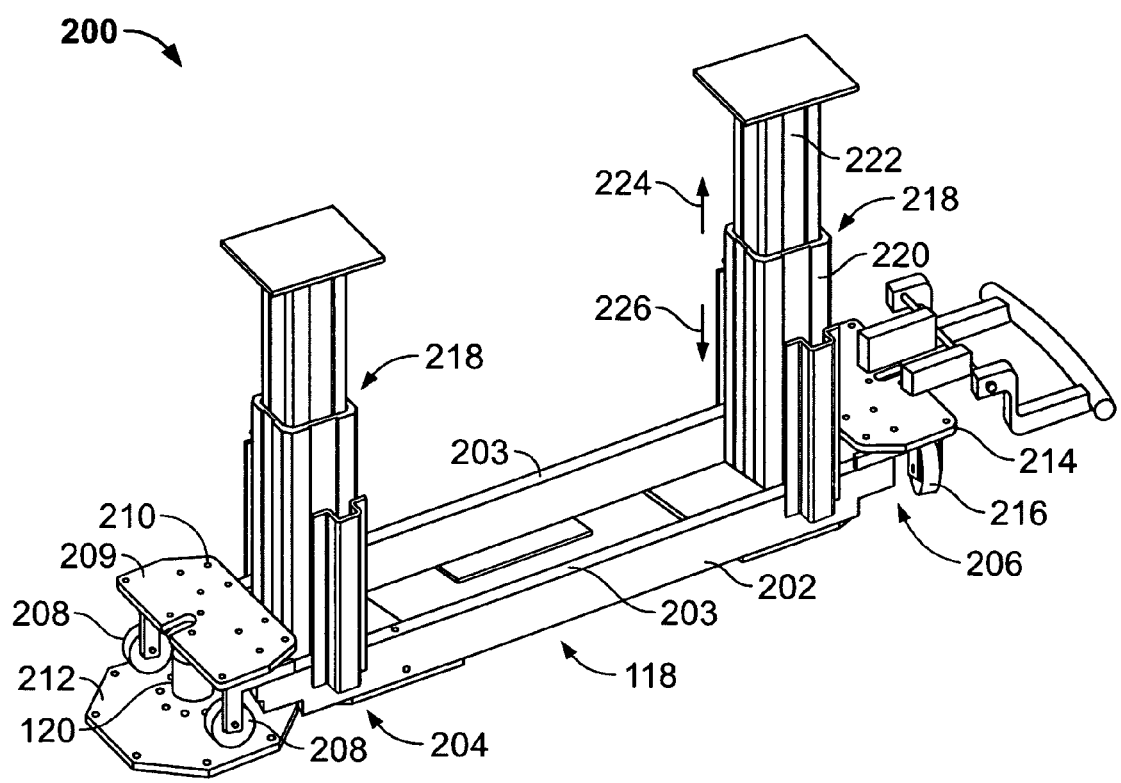
FIG. 2 is a perspective view of an exemplary embodiment of a patient table support mechanism that may be used with the imaging system shown in FIG. 1.

FIG. 2 is a perspective view of an exemplary embodiment of a patient table support mechanism 200 that may be used with imaging system 100 (shown in FIG. 1). Support mechanism 200 includes a chassis 202 including a pair of box-beams 203 extending parallel with respect to each other from a pivot end 204 to a rotating end 206. Pivot end 204 includes pivot 120, a pair of pivot wheels 208, and a pivot support member 209 fixedly coupled between pivot ends 204 of respective box-beams 203. A pivot socket 210 may be fixedly coupled to pivot support member 209 and extending towards base 118. A pivot pin 212 may be fixedly coupled to base 118 and extending towards pivot socket 210 such that pivot pin 212 is rotatably received within pivot socket 210. Rotating end 206 includes a positioner support member 214 fixedly coupled between rotating ends 206 of respective box-beams 203. A pair of rotating end wheels 216 (only one shown in FIG. 2) are coupled to positioner support member 214 and oriented substantially parallel to guide member 110 such that rotating end 206 is permitted to rotate about pivot 120.

Patient table support mechanism 200 includes at least one height adjustment assembly 218 including a stationary base 220 fixedly coupled to the pair of box-beams 203 and extending substantially perpendicularly from box-beams 203. Stationary base 220 is configured to receive a raise/lower piston 222. Stationary base 220 and raise/lower piston 222 are slidably coupled such that raise/lower piston 222 may extend from stationary base 220 in a raise direction 224 or retract into stationary base 220 in a lower direction 226. In the exemplary embodiment, two height adjustment assembly 218 are configured to operate in a coordinated fashion such that each height adjustment assembly 218 may be raised substantially simultaneously at equal rates and in equal distances such that patient table 106 is raised and lowered parallel to base 118 and/or may be raised and lowered at different rates with respect to each other such that patient table 106 may be inclined with respect to base 118.

Figure 3:
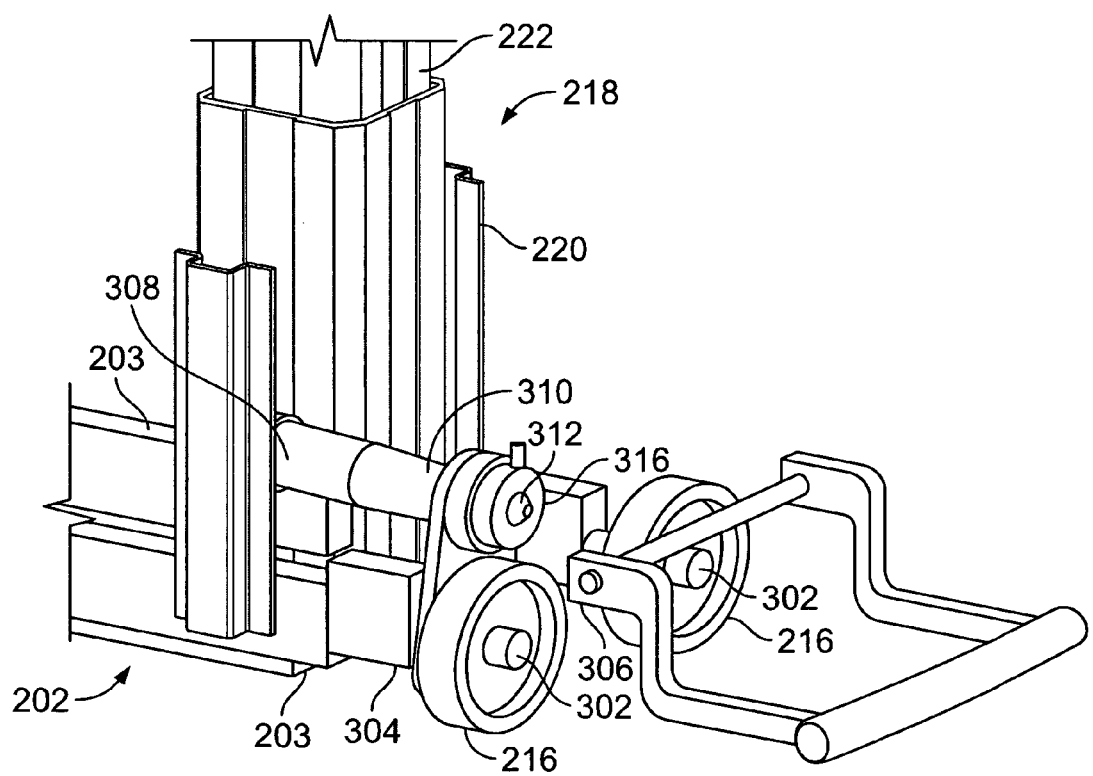
FIG. 3 is an enlarged perspective view of an exemplary embodiment of a rotating end that may be used with the patient table support mechanism shown in FIG. 2.

FIG. 3 is an enlarged perspective view of an exemplary embodiment of rotating end 206 that may be used with patient table support mechanism 200 (shown in FIG. 2). In the exemplary embodiment, rotating end wheels 216 are coupled to chassis 202 through an axle 302. At least one of rotating end wheels 216 includes an axle 302 that includes a sheave 304 configured to receive a belt 306. Belt 306 transmits rotary power from a gear motor 308 through a rotary position encoder 310 and an electromagnetic clutch 312. Gear motor 308 is configured to rotate at selectable speeds in a clockwise (CW) direction 314 and a counter-clockwise (CCW) direction 316 in response to commands and electrical power input from a motion controller (not shown). In an alternative embodiment, sheave 304 is a sprocket configured to receive a chain for transmitting rotary power from gear motor 308 to rotating end wheel 216.

In operation, gear motor 308 may be operated to rotate in a CW direction 316 or CCW direction 318. In one embodiment, rotary position encoder 310 detects the direction, rate of rotation, and an angular displacement of patient table 106 to provide an output signal proportional to a speed and direction of rotation of gear motor 308. Electromagnetic clutch 312 may be selectively variably engaged and disengaged such that a selectable amount of rotational power may be transmitted through electromagnetic clutch 312 to belt 306. Electromagnetic clutch 312 may be activated to engage a brake such that rotating end wheel 216 is prevented from rotating, thereby maintaining patient table 106 in a fixed position.

Figure 4:
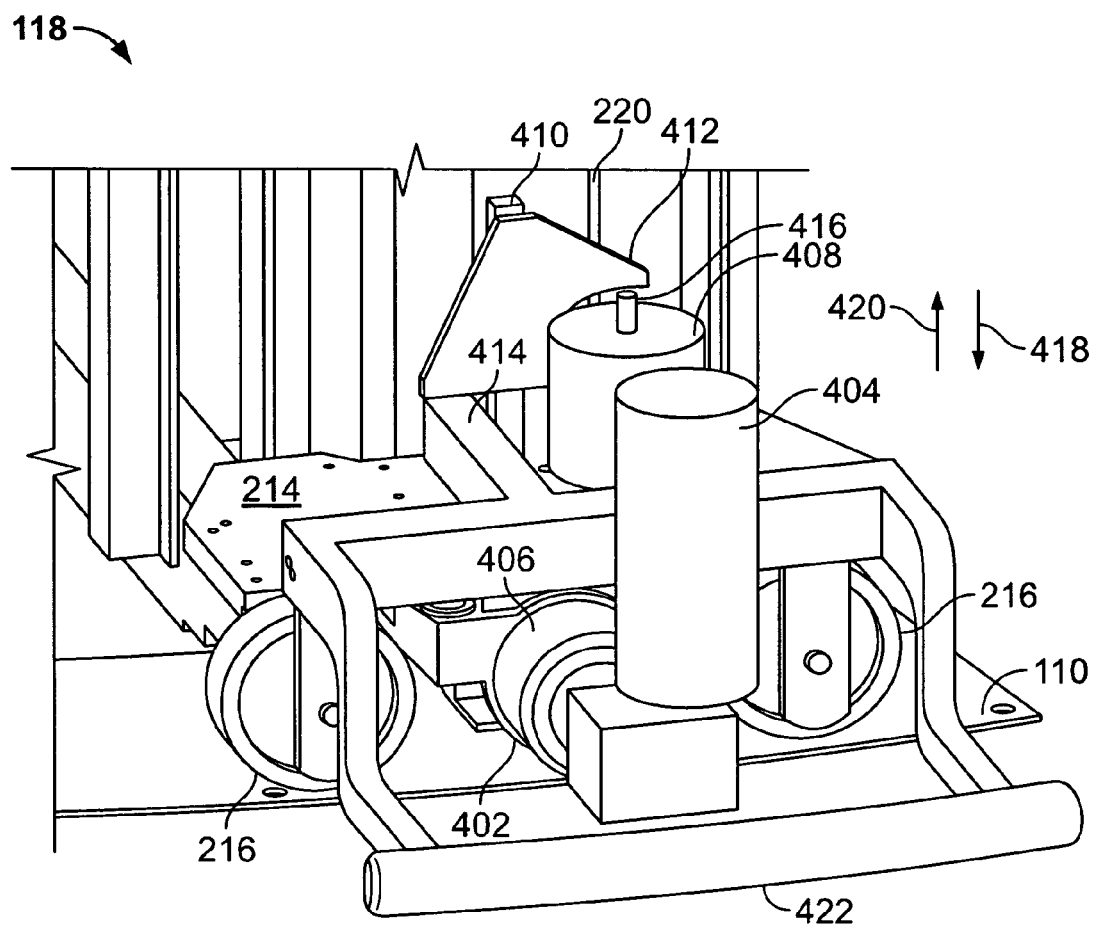
FIG. 4 is an enlarged perspective view of another exemplary embodiment of the rotating end that may be used with the patient table support mechanism shown in FIG. 2.

FIG. 4 is an enlarged perspective view of another exemplary embodiment of rotating end 206 that may be used with patient table support mechanism 200 (shown in FIG. 2). In the exemplary embodiment, rotating end 206 includes at least one driving wheel 402 that is separate from rotating end wheels 216. Driving wheel 402 is biased toward base 118 to increase the amount of friction between driving wheel 402 and base 118 and/or guide member 110. Driving wheel 402 is drivingly coupled to a servo gear motor 404 through a clutch 406. A solenoid 408 is operatively coupled to a positioner connecting rod 410 through an extractor 412 that is pivotally coupled to a manual positioner arm 414. A plunger 416 of solenoid 408 is coupled to extractor 412 such that extending plunger 406 raises positioner connecting rod 410 in direction 418 and retracting plunger 406 lowers positioner connecting rod 410 in direction 420. A positioner pedal 422 is pivotally coupled to extractor 412 such that applying a force in direction 420 raises positioner connecting rod 410 in direction 418.

Figure 5:
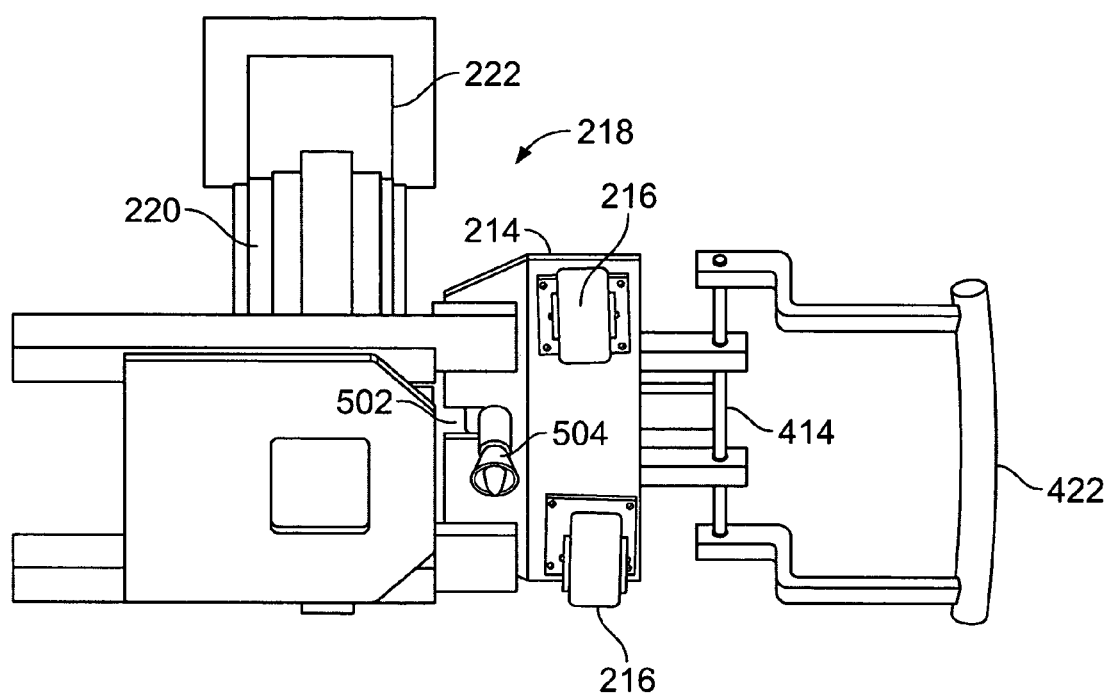
FIG. 5 is a perspective view of the exemplary embodiment of the rotating end shown in FIG. 4 viewed from a base towards a raise/lower piston.

FIG. 5 is a perspective view of the exemplary embodiment of rotating end 206 (shown in FIG. 4) viewed from base 118 towards raise/lower piston 222. Positioner support member 214 includes an aperture 502 therethrough. Positioner connecting rod 410 extends through aperture 502 to a positioner 504 coupled to a distal end 506 of positioner connecting rod 410.

Figure 6:
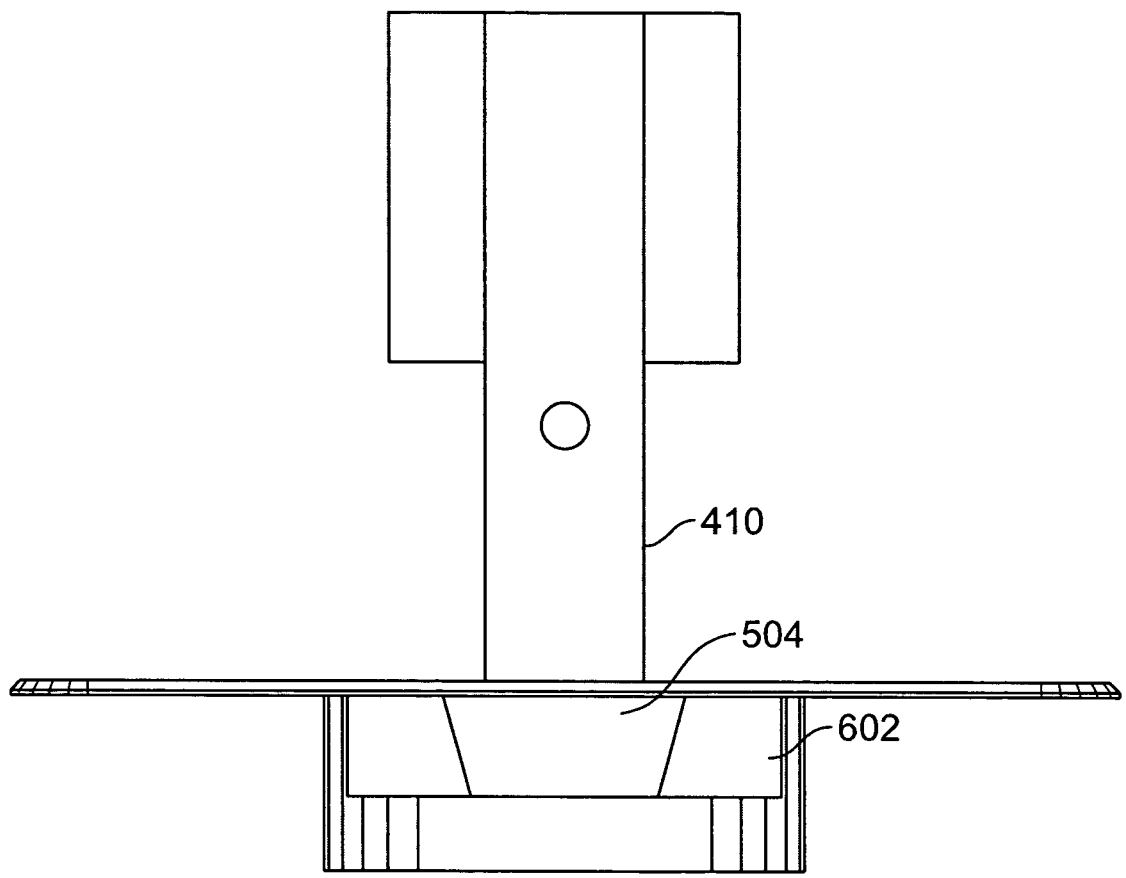
FIG. 6 is an axial elevation view of an exemplary positioner shown in FIG. 5.

FIG. 6 is an axial elevation view of an exemplary positioner 504 (shown in FIG. 5). In the exemplary embodiment, positioner connecting rod 410 couples to a frusto-conically shaped positioner 504 that couples to a complementarily shaped positioning socket 602. The frusto-conical shape of positioner 504 permits positioner 504 to be misaligned with respect to positioning socket 602 when positioner connecting rod 410 is lowered. During a misaligned engagement condition, positioner connecting rod 410 is biased by a spring to accurately locate and lock patient table in the parking positions due to the spring biasing the positioner toward the floor sockets. Solenoid 408, when activating releases the extractor 412 with positioner connecting rod 410 from socket 602 and enable the table to pivot in automatic mode. Solenoid 408 is deactivated in an automatic mode and releases the positioner to the floor, when table approaches the parking position. Patient table 106 continues to move to the parking position in a low speed, positioner connecting rod 410 intrudes into the floor socket 602, comes to its bottom and locks patient table 106 in the parking position. Pedal 422 extracts the extractor 412 with positioner connecting rod 410 from the socket and enables the table to pivot in a manual mode. Pedal 422 is used for emergency or maintenance purposes.

In an alternative embodiment, position connecting rod is biased by solenoid 408 (shown in FIG. 4) such that the biasing force acting between the frusto-conically shaped positioner 504 and socket 602 moves positioner 504 laterally until positioner 504 and socket 602 mate in full engagement such that positioner 504 is fully seated in socket 602 such that patient table 106 is parked in substantial alignment with examination axis 112 or examination axis 114. Parking patient table 106 includes detecting the approximate patient table 106 alignment with respect to examination axis 112 or examination axis 114, stopping rotation of patient table 106 when the approximate patient table alignment is detected, and engaging positioner 504 to a locator, such as positioning socket 602, fixedly coupled in a predetermined location such that the engagement of positioner 504 to the positioning socket 602 positions patient table 106 in substantial alignment with the respective examination axis.

Figure 7:
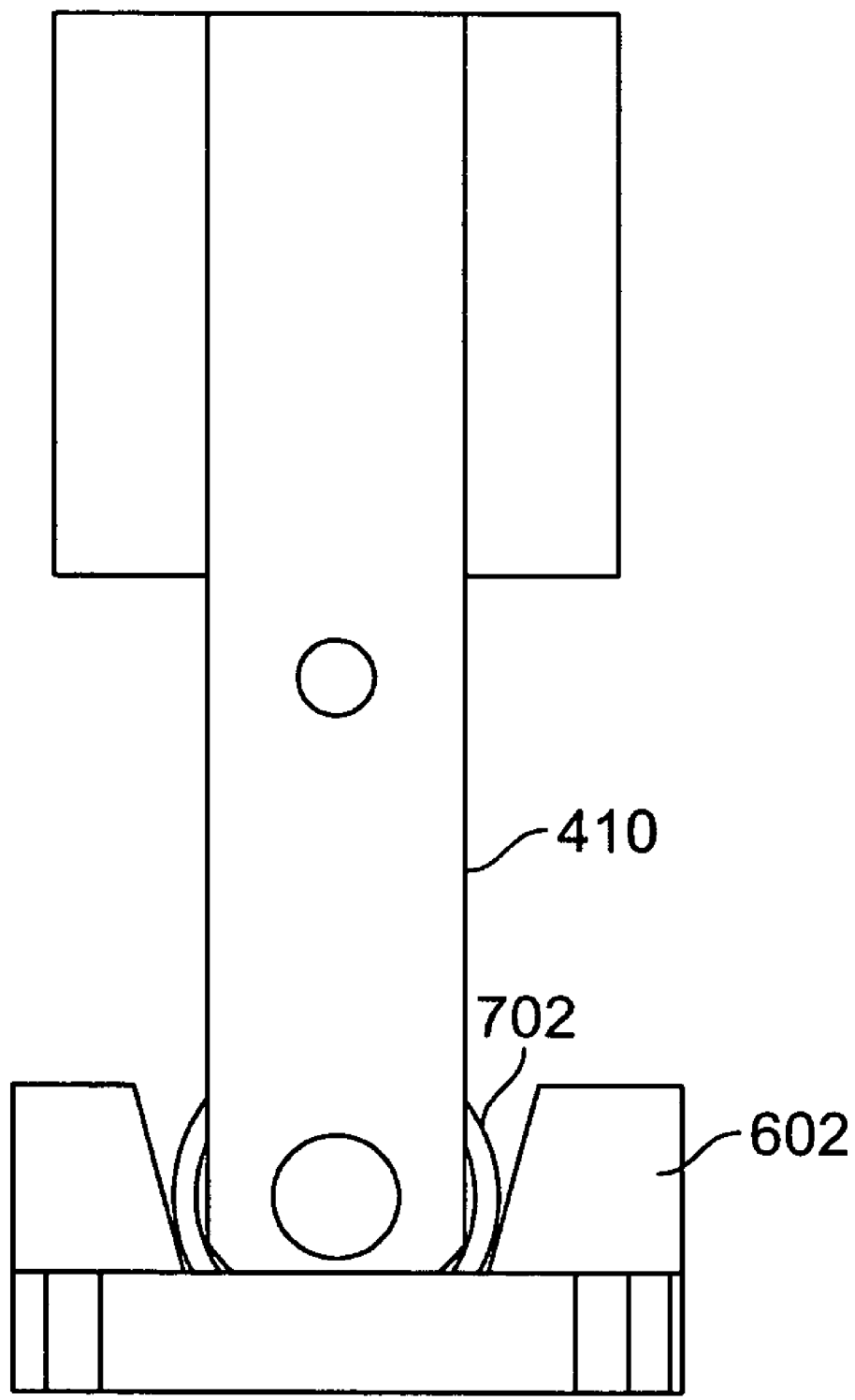
FIG. 7 is an axial elevation view of another exemplary positioner that may be used with the patient table support mechanism shown in FIG. 2.

FIG. 7 is an axial elevation view of another exemplary positioner 702 that may be used with patient table support mechanism 200 (shown in FIG. 2). In the exemplary embodiment, positioner connecting rod 410 couples to a circularly-shaped wheeled positioner 702 that couples to frusto-conically shaped positioning socket 602. The circularly-shaped wheel configuration of positioner 702 permits positioner 702 to be misaligned with respect to positioning socket 602 when positioner connecting rod 410 is lowered. During a misaligned engagement condition, position connecting rod is biased by solenoid 408 (shown in FIG. 4) such that the biasing force between the circularly-shaped wheel configuration of positioner 702 and frusto-conically shaped positioning socket 602 causes positioner 702 to move laterally until positioner 702 and socket 602 mate in full engagement such that positioner 702 is fully engaged in frusto-conically shaped positioning socket 602.

Figure 8:
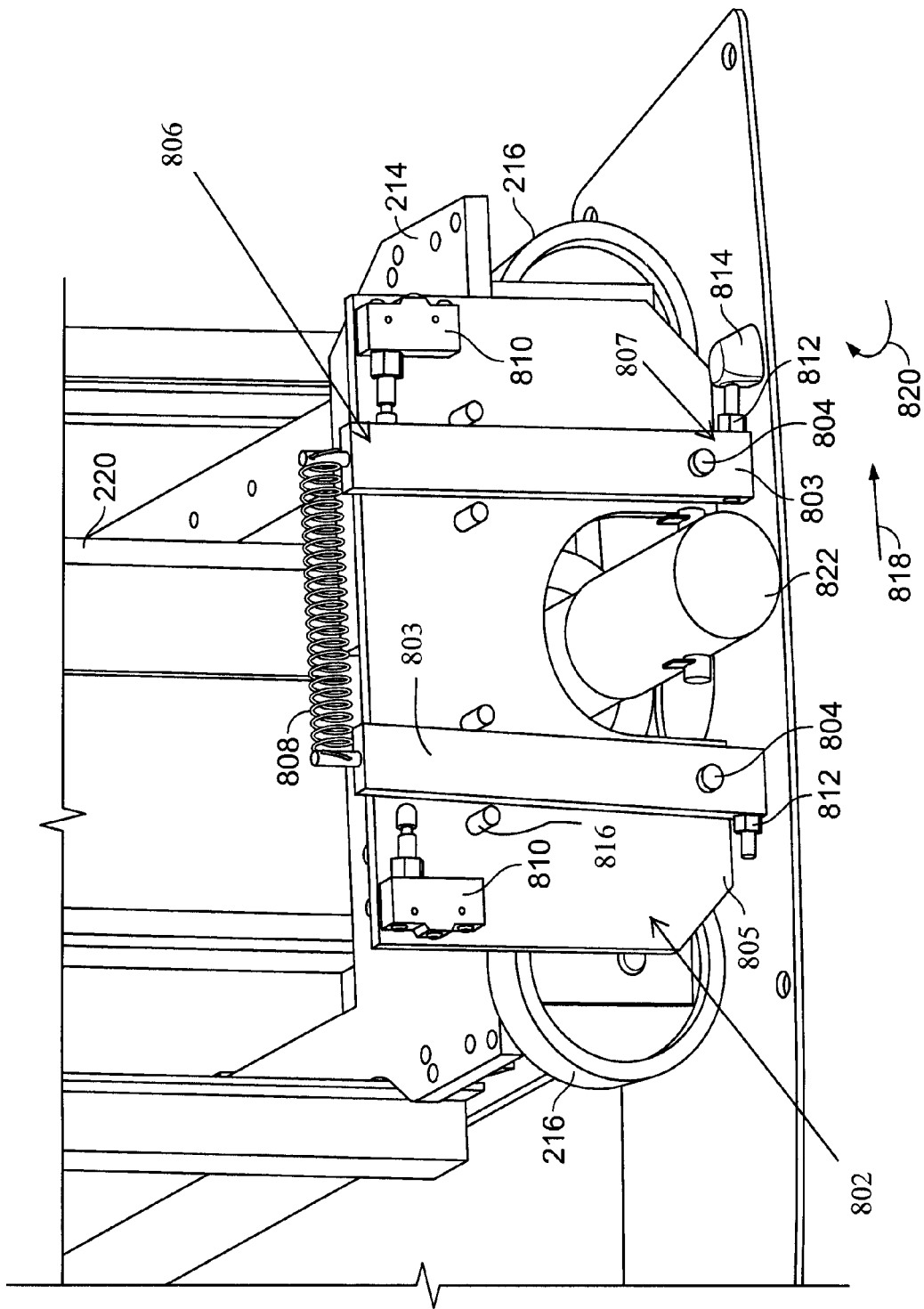
FIG. 8 is an enlarged perspective view of another exemplary embodiment of the rotating end that may be used with the patient table support mechanism shown in FIG. 2.

FIG. 8 is an enlarged perspective view of another exemplary embodiment of rotating end 206 that may be used with patient table support mechanism 200 (shown in FIG. 2). In the exemplary embodiment, rotating end 206 includes a stopping device 802 coupled to rotating end 206. Stopping device 802 includes a support plate 805 coupled to rotating end 206 and at least one stopping lever 803 pivotally coupled to support plate 805 through a stopping pivot 804. An actuation end 806 of stopping lever 803 includes a biasing device 808, for example, a spring to facilitate returning stopping lever 803 to a neutral position after actuation of a limit switch 810 when a respective lever screw 812 contacts a floor hard stopper 814. A plurality of travel stops 816 are coupled to stopping device 802 to limit the travel of stopping lever 803 from an actuation position to the neutral position.

During operation, patient table support mechanism 200 may be moving in a direction 818 for alignment with one of the examination axes, 112 or 114. If rotating end 206 exceeds the predetermined rotational travel distance, lever screw 812 will contact floor hard stopper 814 causing stopping lever 803 to pivot about stopping pivot 804 in a clockwise direction 820, and causing actuation end 806 of stopping lever 803 to engage limit switch 810. In an alternative embodiment, a distal end 807 of stopping lever may extend into a slot recessed into guide 110. If rotating end 206 exceeds the predetermined rotational travel distance, lever screw 812 will contact an end (not shown) of the recessed slot. Limit switch 810 is configured to transmit an overtravel signal to the motion controller (not shown) to stop operation of a planetary servo gear motor 822 that is drivingly coupled to driving wheel 402.

Figure 9:
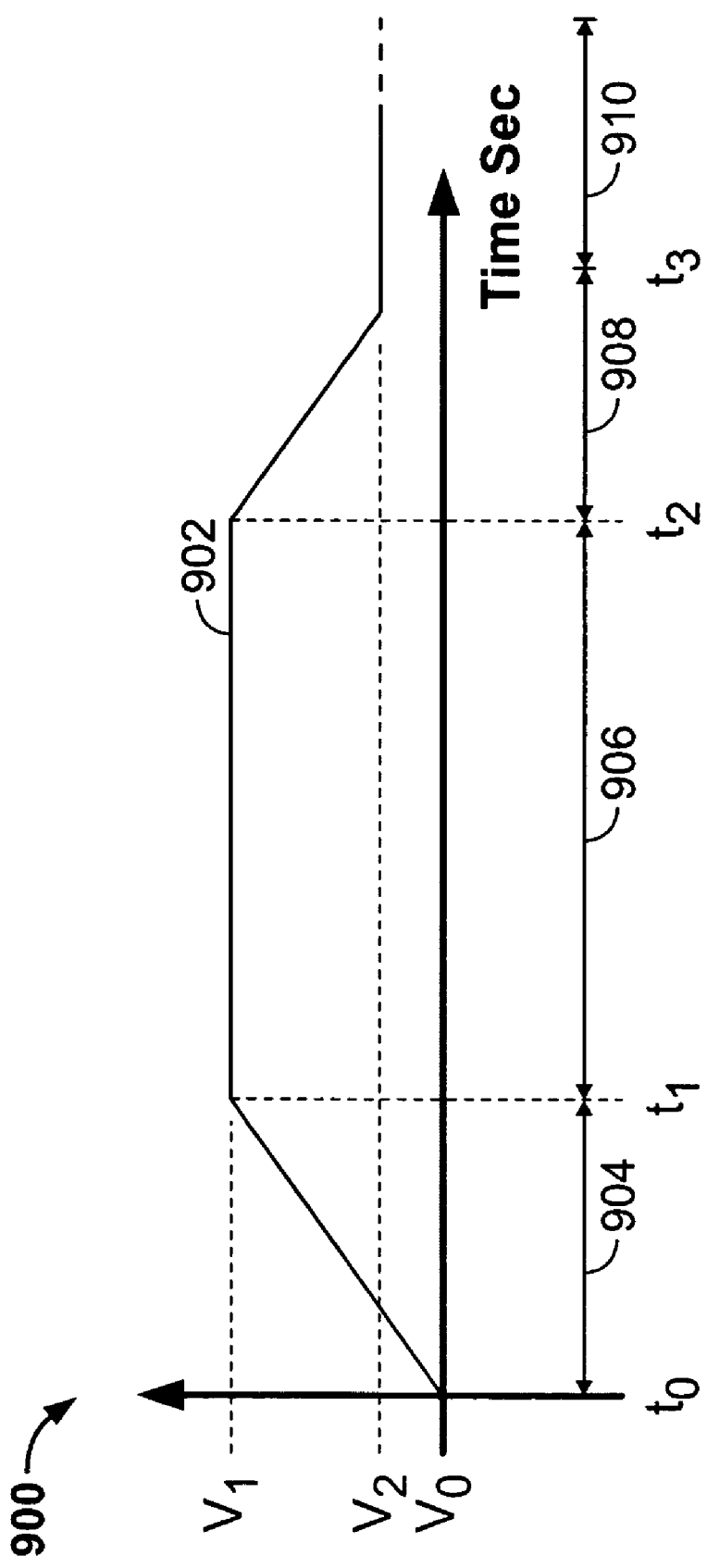
FIG. 9 is a graph of an exemplary trace of angular velocity of rotation of the patient table support mechanism shown in FIG. 2.

FIG. 9 is a graph 900 of an exemplary trace 902 of a predetermined angular velocity profile that may be used to control the speed of rotation of patient table support mechanism 200 (shown in FIG. 2) relative to time during a movement from one examination axis (112 or 114) to the other. Trace 902 includes a first portion 904 that extends from a time $t_0$ to a time $t_1$, a second portion 906 that extends from time $t_1$ to a time $t_2$, a third portion 908 that extends from time $t_2$ to a time $t_3$, and a fourth portion 910 that extends from time $t_3$ to a time when patient table 106 is substantially aligned with a respective examination axis and the driving motor has been deenergized. Portion 904 defines a predetermined acceleration from rest $V_0$ to a predetermined angular velocity $V_1$. The predetermined acceleration value is determined to reduce shifting a patient on patient table 106 due to a rapid acceleration. Portion 906 defines a time period of substantially constant movement angular velocity $V_1$. Third portion 908 illustrates a predetermined deceleration rate from angular velocity $V_1$ to an angular velocity $V_2$. Angular velocity $V_2$ represents a creep velocity that is less than angular velocity $V_1$. Angular velocity $V_2$ may be used proximate the end of rotation of patient table support mechanism 200. The slower velocity allows patient table support mechanism 200 to lower positioner 504 in preparation for engaging positioner 504 into positioning socket 602. When positioner 504 engages positioning socket 602, power to the driving motor is deenergized and patient table support mechanism 200 is locked into a repeatable position in substantial alignment with examination axis 112 or 114.

It is contemplated that the various embodiments of the invention may be implemented with any multi-modality imaging systems, such as, for example, but not limited to, a CT/SPECT imaging system as well as systems having currently known or later developed modalities as well as combinations, such as, for example, but not limited to, a combination SPECT/ultrasound system and/or a CT/MRI system.

The above-described embodiments of multi-modality imaging systems provide a cost-effective and reliable means for examining a patient. Specifically, the acceleration and deceleration selection facilitate reducing shifting a patient location due to changes in momentum of the patient table. Use of a highly repeatable positioner and socket to fix the alignment location permits returning a patient to a substantially known location at each examination axis. Accordingly, the multi-modality imaging systems described above provide for maintaining an accurate registration of images from separate modalities in a cost effective and reliable manner.

An exemplary embodiment of a multi-modality imaging system is described above in detail. The multi-modality imaging system components illustrated are not limited to the specific embodiments described herein, but rather, components of each multi-modality imaging system may be utilized independently and separately from other components described herein. For example, the multi-modality imaging system components described above also may be used in combination with other imaging systems.

While the invention has been described in terms of various specific embodiments, those skilled in the art will recognize that the invention can be practiced with modification within the spirit and scope of the claims.

What is claimed is:

1. An imaging system comprising:
   at least a first and a second imaging assembly configured to obtain medical diagnostic images of a patient for at least first and second imaging modalities, said imaging assemblies being aligned along different first and second examination axes;
   a table configured to support a patient during a first and a second examination; and
   a support mechanism configured to move said table between a first and a second examination position aligned with said first and second examination axes corresponding to said first and a second imaging assemblies, said support mechanism comprising a positioner configured to engage a positioning socket to align said patient table with at least one of said first and second examination axes, wherein said support mechanism is configured to move said table between the first and second examination positions using a predetermined angular velocity profile, wherein the predetermined angular velocity profile comprises a first time period of acceleration, a second time period of an approximately constant angular velocity, and a third time period of deceleration.

2. An imaging system in accordance with claim 1 wherein said support mechanism is configured to move said table about a pivot axis between the first examination axis and the second examination axis.

3. An imaging system in accordance with claim 1 wherein said support mechanism further comprises a rail system configured to guide said table between the first examination axis and the second examination axis.

4. An imaging system in accordance with claim 1 further comprising:
   a stopping device coupled to a rotating end of said support mechanism, wherein said stopping device comprises at least one stopping lever pivotally coupled to said rotating end through a stopping pivot;
   a biasing device coupled to an actuation end of said stopping lever; and
   a limit switch configured to be actuated by said actuation end of said stopping lever when a distal end of said stopping lever contacts a movement stop.

5. An imaging system in accordance with claim 4 further comprising said movement stop, wherein said movement stop comprises at least one of a protuberance and a slot end.

6. An imaging system in accordance with claim 4 wherein said biasing device comprises a spring.

7. An imaging system in accordance with claim 1 wherein the predetermined angular velocity profile comprises at least two different non-zero angular velocities.

8. An imaging system in accordance with claim 1 wherein said support mechanism comprises first and second height adjustment assemblies separately operable to one of raise and lower said table.

9. An imaging system in accordance with claim 1 wherein said positioner is frusto-conically shaped.

10. An imaging system in accordance with claim 1 wherein said positioner comprises a circularly-shaped wheeled member.

11. An imaging system in accordance with claim 1 further comprising said positioning socket, wherein said positioner is complementarily shaped relative to said positioning socket.

12. An imaging system in accordance with claim 1 wherein the predetermined angular velocity profile comprises a non-zero angular acceleration rate.

13. An imaging system in accordance with claim 1 wherein said positioner comprises a frusto-conical shape and extends from said support mechanism when disengaged from the positioning socket.

14. An imaging system in accordance with claim 1 wherein the predetermined angular velocity profile comprises a fourth time period of a second angular velocity that is less than the approximately constant angular velocity.

15. An imaging system in accordance with claim 1 wherein said support mechanism is configured to control at least one of an acceleration and an angular velocity of said table during movement of said table between the first and second examination positions to facilitate reducing shifting of the patient relative to the table during movement of the table between the first and second examination positions.

16. An imaging system comprising:
at least a first and a second imaging assembly configured to obtain medical diagnostic images of a patient for at least first and second imaging modalities, said imaging assemblies being aligned along different first and second examination axes;
a table configured to support a patient during a first and a second examination;
a support mechanism configured to move said table between a first and a second examination position aligned with said first and second examination axes corresponding to said first and a second imaging assemblies, and
a stopping device coupled to a rotating end of said support mechanism, wherein said stopping device comprises at least one stopping lever pivotally coupled to said rotating end.

* * * * *

UNITED STATES PATENT AND TRADEMARK OFFICE
CERTIFICATE OF CORRECTION

PATENT NO.       : 7,613,492 B2                     Page 1 of 1
APPLICATION NO.  : 10/898781
DATED            : November 3, 2009
INVENTOR(S)      : Altman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1028 days.

Signed and Sealed this

Nineteenth Day of October, 2010

David J. Kappos
*Director of the United States Patent and Trademark Office*